(12) United States Patent
Hyland et al.

(10) Patent No.: US 12,040,048 B2
(45) Date of Patent: Jul. 16, 2024

(54) METHODS FOR CONTEXT BASED COMPRESSION OF GENOMIC DATA FOR IMMUNO-ONCOLOGY BIOMARKERS

(71) Applicant: LIFE TECHNOLOGIES CORPORATION, Carlsbad, CA (US)

(72) Inventors: Fiona Hyland, San Mateo, CA (US); Asha Kamat, Reading, MA (US); Timothy Looney, Austin, TX (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 18/170,797

(22) Filed: Feb. 17, 2023

(65) Prior Publication Data

US 2023/0282306 A1 Sep. 7, 2023

Related U.S. Application Data

(63) Continuation of application No. 16/851,472, filed on Apr. 17, 2020, now Pat. No. 11,610,648.
(Continued)

(51) Int. Cl.
*G16B 20/20* (2019.01)
*G06F 16/2457* (2019.01)
(Continued)

(52) U.S. Cl.
CPC ....... *G16B 20/20* (2019.02); *G06F 16/24575* (2019.01); *G06F 16/248* (2019.01); *G06N 3/126* (2013.01)

(58) Field of Classification Search
None
See application file for complete search history.

(56) References Cited

U.S. PATENT DOCUMENTS 11,649,488 B2 * 5/2023 Verhaegh .......... G06N 7/01
702/19
2006/0136145 A1 6/2006 Kao et al.
(Continued)

FOREIGN PATENT DOCUMENTS

CN 107577921 A 1/2018
CN 108368546 A 8/2018
(Continued)

OTHER PUBLICATIONS

Havel Jonathan J et al: "The evolving landscape of biomarkers for checkpoint inhibitor immunotherapy", Nature Reviews, Cancer, Nature Publishing Group, vol. 19, No. 3, Feb. 12, 2019 (Feb. 12, 2019), XP036710886, pp. 133-150.
(Continued)

*Primary Examiner* — Kim T Nguyen
(74) *Attorney, Agent, or Firm* — Carolyn Koenig

(57) ABSTRACT

The method includes compressing numbers of reads data for targeted genes of a gene expression assay performed on a test sample. The targeted genes are organized into categories. Each category represents a functional context associated with the targeted genes in that category. The numbers of reads corresponding to targeted genes each category is compressed to form a compressed value for the category. The compressed value is compared to a baseline value for the category to determine an enrichment or a loss of a signature corresponding to the functional context of the category. The method may include analyzing information from multiple assays performed on the test sample, assigning a score value to each assay result and predicting a response to immune-oncology treatment based on the assigned scores.

20 Claims, 3 Drawing Sheets

Related U.S. Application Data

(60) Provisional application No. 62/835,586, filed on Apr. 18, 2019.

(51) Int. Cl.
*G06F 16/248* (2019.01)
*G06N 3/126* (2023.01)

(56) References Cited

U.S. PATENT DOCUMENTS

| | | | |
|---|---|---|---|
| 2019/0100790 A1* | 4/2019 | Van De Stolpe | C12Q 1/6886 |
| 2020/0152289 A1 | 5/2020 | Cleary et al. | |
| 2020/0335176 A1* | 10/2020 | Hyland | G06N 3/126 |
| 2021/0089358 A1 | 3/2021 | Yeung-Rhee et al. | |
| 2021/0115520 A1* | 4/2021 | Maher | C12Q 1/6886 |
| 2021/0151123 A1 | 5/2021 | Araya et al. | |
| 2021/0365462 A1 | 11/2021 | Pippin et al. | |
| 2023/0053844 A1* | 2/2023 | Chandak | G16B 30/20 |
| 2023/0162815 A1* | 5/2023 | Selkov | G16B 40/00 702/20 |
| 2023/0274800 A1* | 8/2023 | Alberti | G16B 30/10 702/19 |

FOREIGN PATENT DOCUMENTS

| | | |
|---|---|---|
| EP | 1583553 A2 | 10/2005 |
| WO | WO-2018057971 A1 | 3/2018 |

OTHER PUBLICATIONS

PCT/US2020/028663, International Search Report and Written Opinion, dated Jul. 21, 2020, 11 pages.

Zhang J., et al., "Meta-analysis of Pathways of Vaccine-induced Adaptive Immunity in Homo Sapiens," Chinese Journal of Viral Diseases, Sep. 15, 2013, vol. 3, No. 5, pp. 343-348.

* cited by examiner

METHODS FOR CONTEXT BASED COMPRESSION OF GENOMIC DATA FOR IMMUNO-ONCOLOGY BIOMARKERS

CROSS-REFERENCE

This application is a continuation of U.S. application Ser. No. 16/851,472 filed Apr. 17, 2020, which claims priority to U.S. application No. 62/835,586 filed Apr. 18, 2019, which disclosures are herein incorporated by reference in their entirety.

BACKGROUND

Nucleic acid sequencing data may be obtained in various ways, including using next-generation sequencing systems such as, for example, the Ion PGM™, Ion Proton™, and Ion S5™ systems implementing Ion Torrent™ sequencing technology (see, e.g., U.S. Pat. No. 7,948,015, issued May 24, 2011, U.S. Pat. Appl. Publ. No. 2010/0137143, published Jun. 3, 2010, U.S. Pat. Appl. Publ. No. 2009/0026082, published Jan. 29, 2009, and U.S. Pat. Appl. Publ. No. 2010/0282617, published Nov. 11, 2010, which are all incorporated by reference herein in their entirety). Such next-generation sequencing systems may be used in conjunction with primers for targets of interest, which primers may be designed or prepared in various ways, including as described in U.S. Pat. Appl. Publ. No. 2012/0295819, published Nov. 22, 2012, which is incorporated by reference herein in its entirety.

Anti-cancer response to immune-therapeutics can be dramatic. However, anti-cancer response may be observed only in a subset of tumors. Ongoing research is directed to determining why some cancers do not respond to immune-therapeutics. One of the key determinants of response is the tumor micro environment. Current research has demonstrated that the pre-existing immune contexture of tumors contributes significantly to response to immunotherapeutic agents. Therefore, there is a need for improved methods for determining genes essential for immune profiling of the tumor environment and for generating immune profiles that determine the immune status of the tumor.

SUMMARY

Extensive and comprehensive mining of literature can be used to determine the genes that provide an overview of the immunological patterns of tumors. Public tools such as DAVID (Database for Annotation, Visualization and Integrated Discovery, www.david.ncifcrf.gov/) can be used to determine the functional attributes of these genes. A panel of these genes and next generation sequencing (NGS) based gene expression technology can be used to generate expression based functional characterization of tumors.

Large amounts of nucleic acid sequence data, obtained from a nucleic acid sample using various techniques, platforms or technologies, may be stored and processed for detection of biomarkers relevant to prediction of a response to immuno-oncology treatment. There is a need for new methods, systems and computer readable media that compress nucleic acid sequence read data for genes associated with immuno-oncology biomarkers, to reduce memory requirements for storage, and to detect enrichment or loss of a signature corresponding to the functional context based on the compressed data. There is a need for new methods, systems and computer readable media for analyzing results information from multiple assays to predict a response to immuno-oncology treatments.

According to an exemplary embodiment, there is provided a method, comprising: (a) receiving a plurality of numbers of reads for a plurality of targeted genes of a gene expression assay performed on a test sample. The plurality of targeted genes is organized into a plurality of categories. A $k^{th}$ category of the plurality of categories represents a functional context associated with the targeted genes in the $k^{th}$ category. The $k^{th}$ category has $N_k$ numbers of reads associated with $N_k$ targeted genes of the plurality of targeted genes. For each $k^{th}$ category in the plurality of categories, the method applies the steps: (b) determining a number of reads of the $N_k$ numbers of reads for each $i^{th}$ targeted gene in the $k^{th}$ category; (c) compressing the $N_k$ numbers of reads in the $k^{th}$ category to form a compressed value for the $k^{th}$ category, wherein the compressed value has a reduced amount of data for the $k^{th}$ category for storing in a memory; and (d) comparing the compressed value to a baseline value for the $k^{th}$ category to determine an enrichment or a loss of a signature corresponding to the functional context of the $k^{th}$ category.

According to an exemplary embodiment, there is provided a system, comprising a processor and a memory communicatively connected with the processor, the processor configured to perform a method including: a) receiving a plurality of numbers of reads for a plurality of targeted genes of a gene expression assay performed on a test sample. The plurality of targeted genes is organized into a plurality of categories. A $k^{th}$ category of the plurality of categories represents a functional context associated with the targeted genes in the $k^{th}$ category. The $k^{th}$ category has $N_k$ numbers of reads associated with $N_k$ targeted genes of the plurality of targeted genes. For each $k^{th}$ category in the plurality of categories, the processor applies the steps: (b) determining a number of reads of the $N_k$ numbers of reads for each targeted gene in the $k^{th}$ category; (c) compressing the $N_k$ numbers of reads in the $k^{th}$ category to form a compressed value for the $k^{th}$ category, wherein the compressed value has a reduced amount of data for the $k^{th}$ category for storing in the memory; and (d) comparing the compressed value to a baseline value for the $k^{th}$ category to determine an enrichment or a loss of a signature corresponding to the functional context of the $k^{th}$ category.

According to an exemplary embodiment, there is provided a non-transitory machine-readable storage medium comprising instructions which, when executed by a processor, cause the processor to perform a method, comprising: a) receiving a plurality of numbers of reads for a plurality of targeted genes of a gene expression assay performed on a test sample. The plurality of targeted genes is organized into a plurality of categories. A $k^{th}$ category of the plurality of categories represents a functional context associated with the targeted genes in the $k^{th}$ category. The $k^{th}$ category has $N_k$ numbers of reads associated with $N_k$ targeted genes of the plurality of targeted genes. For each $k^{th}$ category in the plurality of categories, the processor applies the steps: (b) determining a number of reads of the $N_k$ numbers of reads for each targeted gene in the $k^{th}$ category; (c) compressing the $N_k$ numbers of reads in the $k^{th}$ category to form a compressed value for the $k^{th}$ category, wherein the compressed value has a reduced amount of data for the $k^{th}$ category for storing in a memory; and (d) comparing the compressed value to a baseline value for the $k^{th}$ category to determine an enrichment or a loss of a signature corresponding to the functional context of the $k^{th}$ category.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

DETAILED DESCRIPTION

Figure 1:
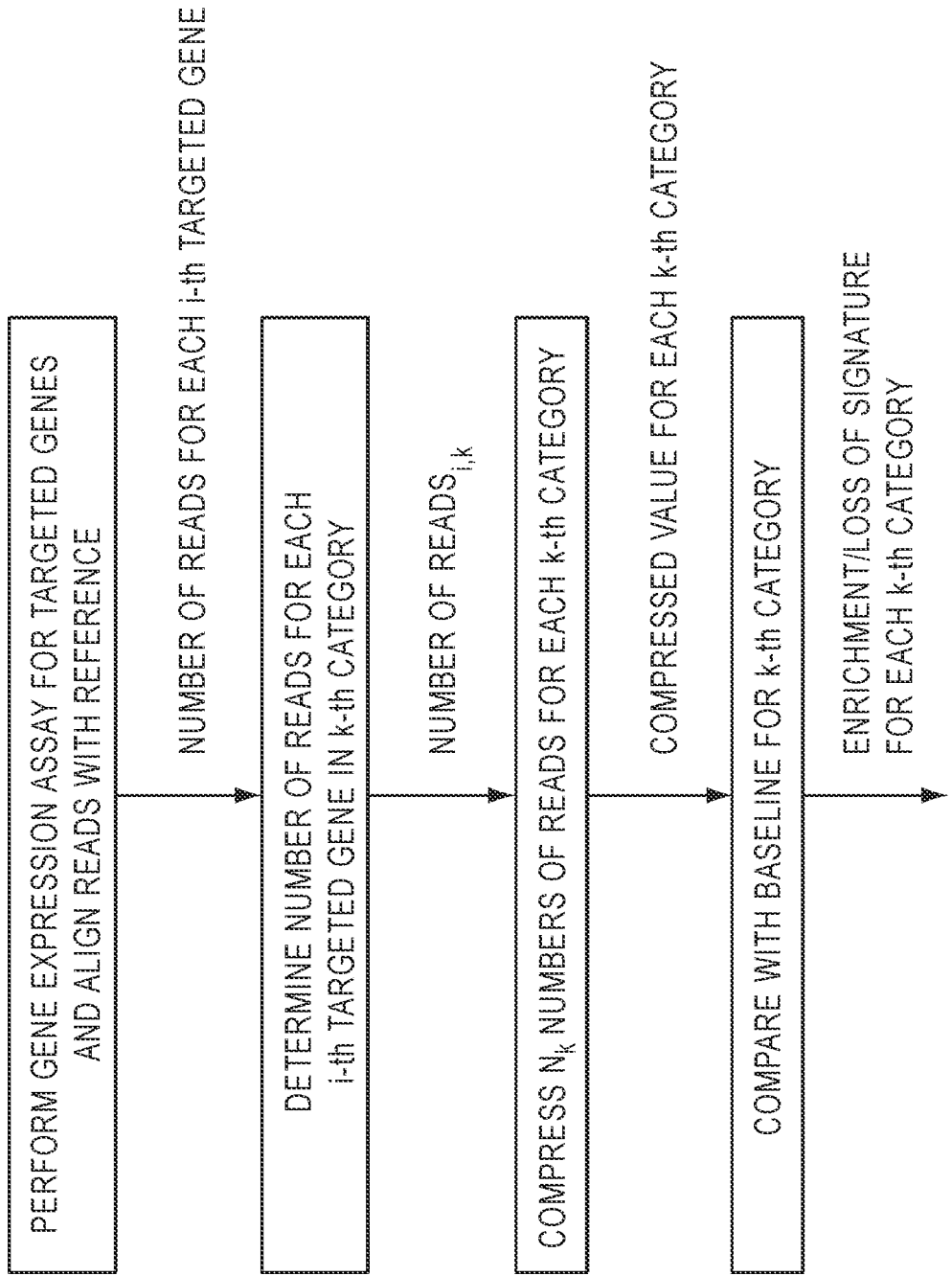
FIG. 1 is a block diagram of compression and analysis of numbers of reads for targeted genes in categories associated with functional contexts, in accordance with an exemplary embodiment.

In accordance with the teachings and principles embodied in this application, new methods, systems and non-transitory machine-readable storage medium are provided to compress data of nucleic acid sequence reads for genes associated with immune-oncology biomarkers and to detect enrichment or loss of a signature corresponding to the functional context based on the compressed data. New methods, systems and non-transitory machine-readable storage medium are provided for analyzing results information from multiple assays to predict a response to immuno-oncology treatment.

In various embodiments, DNA (deoxyribonucleic acid) may be referred to as a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. In various embodiments, "nucleic acid sequencing data," "nucleic acid sequencing information," "nucleic acid sequence," "genomic sequence," "genetic sequence," or "fragment sequence," "nucleic acid sequence read" or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, for example 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The phrase "genomic variants" or "genome variants" denote a single or a grouping of sequences (in DNA or RNA) that have undergone changes as referenced against a particular species or sub-populations within a particular species due to mutations, recombination/crossover or genetic drift. Examples of types of genomic variants include, but are not limited to: single nucleotide polymorphisms (SNPs), copy number variations (CNVs), insertions/deletions (Indels), inversions, etc.

In various embodiments, genomic variants can be detected using a nucleic acid sequencing system and/or analysis of sequencing data. The sequencing workflow can begin with the test sample being sheared or digested into hundreds, thousands or millions of smaller fragments which are sequenced on a nucleic acid sequencer to provide hundreds, thousands or millions of sequence reads, such as nucleic acid sequence reads. Each read can then be mapped to a reference or target genome, and in the case of mate-pair fragments, the reads can be paired thereby allowing interrogation of repetitive regions of the genome. The results of mapping and pairing can be used as input for various standalone or integrated genome variant (for example, SNP, CNV, Indel, inversion, etc.) analysis tools.

The phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization.

The phrase "sample genome" can denote a whole or partial genome of an organism.

As used herein, a "targeted panel" refers to a set of target-specific primers that are designed for selective amplification of target gene sequences in a sample. In some embodiments, following selective amplification of at least one target sequence, the workflow further includes nucleic acid sequencing of the amplified target sequence.

As used herein, "target sequence" or "target gene sequence" and its derivatives, refers to any single or double-stranded nucleic acid sequence that can be amplified or synthesized according to the disclosure, including any nucleic acid sequence suspected or expected to be present in a sample. In some embodiments, the target sequence is present in double-stranded form and includes at least a portion of the particular nucleotide sequence to be amplified or synthesized, or its complement, prior to the addition of target-specific primers or appended adapters. Target sequences can include the nucleic acids to which primers useful in the amplification or synthesis reaction can hybridize prior to extension by a polymerase. In some embodiments, the term refers to a nucleic acid sequence whose sequence identity, ordering or location of nucleotides is determined by one or more of the methods of the disclosure.

As used herein, "target-specific primer" and its derivatives, refers to a single stranded or double-stranded polynucleotide, typically an oligonucleotide, that includes at least one sequence that is at least 50% complementary, typically at least 75% complementary or at least 85% complementary, more typically at least 90% complementary, more typically at least 95% complementary, more typically at least 98% or at least 99% complementary, or identical, to at least a portion of a nucleic acid molecule that includes a target sequence. In such instances, the target-specific primer and target sequence are described as "corresponding" to each other. In some embodiments, the target-specific primer is capable of hybridizing to at least a portion of its corresponding target sequence (or to a complement of the target sequence); such hybridization can optionally be performed under standard hybridization conditions or under stringent hybridization conditions. In some embodiments, the target-specific primer is not capable of hybridizing to the target sequence, or to its complement, but is capable of hybridizing to a portion of a nucleic acid strand including the target sequence, or to its complement. In some embodiments, a forward target-specific primer and a reverse target-specific primer define a target-specific primer pair that can be used to amplify the target sequence via template-dependent primer extension. Typically, each primer of a target-specific primer pair includes at least one sequence that is substantially complementary to at least a portion of a nucleic acid molecule including a corresponding target sequence but that is less than 50% complementary to at least one other target sequence in the sample. In some embodiments, amplification can be performed using multiple target-specific primer pairs in a single amplification reaction, wherein each primer pair includes a forward target-specific primer and a reverse target-specific primer, each including at least one sequence that substantially complementary or substantially identical to a corresponding target sequence in the sample, and each primer pair having a different corresponding target sequence.

In some embodiments, a gene expression panel such as, Oncomine Immune Response Research Assay (OIRRA), uses approximately 400 genes to characterize solid tumors and the tumor microenvironment. The OIRRA panel is available from ThermoFisher Scientific (SKU A32881 and A32928). Compositions and methods for assessing immune response are described in PCT international publication number WO 2018/057971, published 29 Mar. 2018, incorporated by reference herein in its entirety. Analysis of the expression of these genes can reveal distinct characteristics of the tumor microenvironment, including immune-active, the opposing immune desert phenotype, and an intermediate phenotype, immune-excluded. Additional phenotypes describing specific properties of the tumor microenvironment and the immune system can be predicted. In some embodiments, the methods described herein provide insights into the tumor environment by generating several signatures associated with response. The utility of this assay in biomarker research includes the ability to generate immune related signatures that allow for identifying tumors that are likely to respond to immunotherapy.

In some embodiments, one or more of the categories shown in Table 1 may be selected for a signature associated with a collection of genes based on information from the literature. A category corresponds to a signature, or functional context associated with the collection of genes. Typically, genes identified will be upregulated for tumors that are a member of the category identified, unless otherwise noted in the table. The term upregulation refers to a level of expression of a gene that is at least double the expression of that gene in normal tissue. The term downregulation refers to a level of expression of a gene that is less than half the expression of that of the gene in normal tissue. The term dendritic cell (DC) maturation indicates that the cells have matured to form dendritic cells.

TABLE 1

| CATEGORY | GENES |
| --- | --- |
| Immune Inflamed | CCL5, CXCL9, CD27, CXCR6, IDO1, STAT1, TIGIT, CD8A, LAG3, CD274, PDCD1LG2, CD276, HLA-E, NKG7, PSMB10, HLA-DRB1, HLA-DQA1, CMKLR1, CD8A, PD-L1, IL-18, CXCL11, CTLA4, CD3D, CD3E, CD3G, CD4, CD8B, CD19-1, CD19-2 |
| IFNG Signature | IFN-G, IDO1, CXCL10, CXCL9, HLA-DRA, STAT1 |
| Immune Excluded | IDO1, CIITA, CD3E, CCL5, GZMK, CD2, HLA-DRA, CXCL13, IL2RG, NKG7, HLA-E, CXCR6, LAG3, CXCL10, STST1, GZMB |
| Immune Escape | IL-10, CSF1, VEGF, TGFb, IDO1, FoxP3, MDSC (CD11B, CD33, CD14, TLR-2, -3, -4, and -7, STAT1, STAT3, STAT6, NFKB, ARG1, IDO1, CD40, FUT4), PD-L1 DOWNREGULATION: CD4 + CD25 + FOXP3, CXCR1, CXCR2, CXCL8, CCR2, CXCR4, CCL2, CXCL5, CXCL12, CCR10, CCL22, CCL28, CCL20, CCR6, IL22) DC Maturation: (CD3-, cd14-cd19-cd56-, cd66-, cd11a, cd11c, cd50 (ICAM-2), cd54 (ICAM-1), Cd58 (LFA-3), cd102 (ICAM-3), CD80(B7.1), CD86 (B7.2), CD83, CMRF-44 |
| T cell Trafficking | CXCR3, CXCL9, CXCL10, CXCL11, ICAM1, ICAM2, VEGF, VCAM, IL-10 |
| Immune Desert | Upregulation of CX3CL1, IL-6 |

In some embodiments, one or more categories may be selected from categories related to tumor activity, such as the examples listed in Table 2.

TABLE 2

| CATEGORY | GENES |
| --- | --- |
| Tumor Activity | Genes related to: Release of cancer antigens—Tumor antigens Cell cycle Proliferation—associated with cancer, cell migration and adhesion |

TABLE 2-continued

| CATEGORY | GENES |
| --- | --- |
| | Tumor promoting inflammation |
| | Apoptosis |
| Tumor | Genes related to: |
| Microenvironment | Angiogenesis |
| (TME) | Extracellular Matrix |
| | Collagens |

In some embodiments, one or more categories may be selected from categories related to cell type scoring, such as the examples listed in Table 3.

TABLE 3

| CATEGORY | GENES |
| --- | --- |
| Immunoscore—ratios of immune markers | CD3/CD8, CD3/CD8/CD20/FOXP3, CD3/CD8/CD45RO, CD4/CD8/CD68, CD3/CD8/CD20, CD3/GZMB, CD8/FoxP3 CD8/IL17 DC—CD8alpha+, CD103+ |
| Cell type abundance score | B cells, CD45, CD8, Cytotoxic T, DC, Exhausted CD8, Macrophages, Neutrophils, NKCD56, NK, Th1 (T-bet), Treg (FoxP3) |

In some embodiments, one or more categories may be selected from categories related to stages of the cancer immunity cycle, such as the examples listed in Table 4.

TABLE 4

| CATEGORY | GENES |
| --- | --- |
| Antigen presentation | CD4, CD40, CD40L |
| Priming and activation | PD-1, PD-L1, PD-L2, IL2R, NCAM, GITR, ox40, CD27, CD28, CD127, CD137 |
| Recognition and killing of cancer cells | PD-1, PD-L1, PD-L2, BTLA, HLA-DRA |
| Immune Modulation | ICOS, KIR3DL1, NKp46, CTLA-4, CD3E, CD8A, CD14, CD33, CD68, CD153, CD45RO, NTSE |

In some embodiments, one or more categories may be selected from categories related to the degree of immunogenicity of the tumor, such as the examples listed in Table 5.

TABLE 5

| Higly immunogenic Tumor | TMB value is >17 and/or MSI status is high |
| Moderately immunogenic Tumor | TMB value is between 10 and 17 and/or MSI status is MSI-H |
| Most likely non-immunogenic Tumor | TMB value is less than 10 and MSI-status is MSI-S or MSI-L |

In some embodiments, a baseline expression is determined for each gene of interest. For example, a baseline expression may be determined for each of one or more genes targeted by the OIRRA panel. Establishing a baseline may use data available from public sources as well as data generated from testing of normal samples. Publicly available databases, such as GTEx (Genotype-Tissue Expression, www.gtexportal.org), TCGA (The Cancer Genome Atlas, www.tcga-data.nci.nih.gov), ICGC (International Cancer Genome Consortium, www.icgc.org), and CCLE (Cancer Cell Line Encyclopedia, www.portals.broadinstitute.org/ccle, www.docs.cancergenomicscloud.org/docs/ccle), are generated from data obtained using an Illumina sequencing device (Illumina, San Diego, CA). For data obtained using different sequencing devices, for example data obtained using an Illumina sequencing device and data obtained using an Ion Torrent sequencing device (ThermoFisher Scientific), a transformation function can be determined to compensate for any differential biases in the data that may be due to the type of sequencing device. The baseline number of reads per gene may be determined by averaging numbers of reads that aligned with the gene of interest in multiple tests of normal samples. Applying the transformation function to the data from tests performed on normal samples by a different type of sequencing device may provide comparable data on numbers of reads for determining the baseline number of reads per gene. The advantage of using the numbers of reads from multiple tests on multiple devices is to provide a larger data set of normal samples for a more accurate estimate of the baseline number of reads per gene.

In some embodiments, determining the transformation function T that maps data measured by a first sequencing device (for example an Illumina sequencing device) to analogous data from a second and different sequencing device (for example an Ion Torrent sequencing device) may include the following:

For each targeted gene:
1) Test a plurality of normal samples using the first sequencing device to generate a plurality of numbers of reads for each targeted gene.
2) Average the numbers of reads per targeted gene generated to give a first average number of reads per gene for the first sequencing device, $\text{mean}_{device1}$.
3) Test a plurality of normal samples using the second sequencing device to generate a plurality of numbers of reads for each targeted gene.
4) Average the numbers of reads per targeted gene generated to give a second average number of reads per gene for the second sequencing device, $\text{mean}_{device2}$.
5) Calculate the transformation function T as follows:
    a) Apply curve-fitting to determine parameters of transformation T so that $$\text{mean}_{device2} = T[\text{mean}_{device1}] \qquad (1)$$

$$\text{Error} = \text{mean}_{device2} - \text{mean}_{device1} \qquad (2)$$

b) For example, the parameters of T may be determined based on a minimum mean squared error criterion to achieve a fit to a linear, polynomial or exponential function.

The transformation function may be applied to data on numbers of reads for targeted genes generated by the first sequencing device to give the comparable numbers of reads that would be generated by the second sequencing device.

$$\text{number of reads}_{device2} = T[\text{number of reads}_{device1}] \qquad (3)$$

Using the transformation T to compensate for biases, the numbers of reads available from different sequencing devices are comparable. For example, data on numbers of reads for genes retrieved from GTEx and TCGA public data bases were generated using an Illumina sequencing device. These data may be transformed using equation (3) to provide equivalent numbers of reads for an Ion Torrent sequencing device, for example. The data may increase the number of measurements of normal samples available for calculating the baseline per gene.

In some embodiments, a baseline value for an $i^{th}$ targeted gene, baseline (gene), in normal samples can be determined as follows:

For each i$^{th}$ targeted gene:
1) Retrieve data from a database on numbers of reads$_{device1}$ for the gene of normal samples measured using the first sequencing device (e.g. an Illumina sequencing device). The data base contains a plurality of numbers of reads$_{device1}$ for the i$^{th}$ gene measured from a plurality of normal samples.
2) Transform the numbers of reads$_{device1}$ for the gene to comparable number of read values for the second sequencing device (e.g. an Ion Torrent sequencing device) by T[number of reads$_{device1}$]=number of reads$_{device2}$. This step produces a plurality of numbers of reads$_{device2}$ for the i$^{th}$ gene.
3) Average over the plurality of the numbers of reads$_{device2}$ to establish a baseline value for each gene to give baseline (gene$_i$). The average may be calculated over the numbers of reads$_{device2}$ determined from the transform of step 2) along with numbers of reads$_{device2}$ obtained using device2.

In some embodiments, a baseline value per category, baseline$_k$ may be determined as follows:

For a k$^{th}$ category:
1) Average the baseline values, baseline (gene$_{i,k}$), over all the genes in the k$^{th}$ category:

baseline_mean$_k$=SUM[baseline(gene$_{i,k}$)]/N$_k$ (4)

where N$_k$ is the number of genes in the k$^{th}$ category.
2) Determine the median of the baseline values, baseline (gene$_{i,k}$), for the genes in k$^{th}$ category to give a median baseline value, baseline_median$_k$.
3) Calculate a baseline$_k$ for each category of interest. The baseline$_k$ may be set to baseline_mean$_k$ or baseline_median$_k$. Alternatively, both baseline_mean$_k$ and baseline_median$_k$ may be used.

FIG. 1 is a block diagram of compression and analysis of numbers of reads for targeted genes in categories associated with functional contexts. In some embodiments, an unknown sample may be tested using the second sequencing device, e.g. an Ion Torrent sequencing device, and the numbers of reads$_{device2}$ may be compressed and analyzed to determine enrichment or loss in the test samples with respect to the selected categories of interest, as follows:
1) Test sample for targeted genes, for example by OIRRA panel.
2) Align reads with reference sequence. The aligned sequence reads can be received from a file using a BAM file format, for example. The aligned sequence reads may correspond to a plurality of targeted genes in the sample genome.
3) Determine the number of reads$_{i,k}$ aligned with i$^{th}$ gene in the k$^{th}$ category.
4) Compress the data for numbers of reads$_{i,k}$ in the k$^{th}$ category to form a compressed value for the k$^{th}$ category by calculating a median value and/or a mean value:

median$_k$=median value[numbers of reads$_{i,k}$ for genes$_{i,k}$ in k$^{th}$ category] (5)

mean$_k$=SUM[numbers of reads$_{i,k}$ for genes$_{i,k}$ in k$^{th}$ category]/N$_k$ (6)

where N$_k$ is the number of genes$_{i,k}$ in the k$^{th}$ category. This step compresses the data for the numbers of reads$_{i,k}$ in the k$^{th}$ category by a compression ratio of N$_k$:1 if only one compressed value, either the median$_k$ or mean$_k$ is calculated, or by a compression ratio of N$_k$:2, if two compressed values including both the median$_k$ or mean$_k$ are calculated. The compressed data for the k$^{th}$ category may comprise the median$_k$ or the mean$_k$ or both the median$_k$ and mean$_k$. The k$^{th}$ category represents the context for the context based compression of the numbers of reads$_{i,k}$ for the genes$_{i,k}$ in k$^{th}$ category.
5) For each k$^{th}$ category of interest, compare the compressed data to the baseline$_k$ for the k$^{th}$ category:
   a. If mean$_k$>=Baseline_mean$_k$ report enrichment of signature corresponding to k$^{th}$ category.
   b. If median$_k$>=Baseline_median$_k$ report enrichment of signature corresponding to k$^{th}$ category.
   c. If mean$_k$<Baseline_mean$_k$ report loss of signature corresponding to k$^{th}$ category.
   d. If median$_k$<Baseline_median$_k$ report loss of signature corresponding to k$^{th}$ category.

The compression ratios of N$_k$: 1 or N$_k$:2 directly relate to a reduction in the amount of memory required to store the numbers of reads for each of the categories from the amount of memory required to store the original numbers of reads N$_k$. The compressed value for each k$^{th}$ category has a reduced amount of data for storing in the memory. In some embodiments, the methods described herein may be performed or implemented at least partly using a distributed, clustered, remote, or cloud computing resource. Compression of the number of reads data provides advantages for transmitting the data to processors in a distributed, clustered, remote, or cloud computing resource. Since the volume of data is reduced, the bandwidth and/or time required for transmission across the data transfer interfaces between computing resources is reduced.

In some embodiments, reports for the enrichment or loss of signature may be output for each k$^{th}$ category of interest. Information from the reports of enrichment or loss of signature for the selected categories may be combined with information derived from results of one or more other assays performed on the test sample. A prediction about a response to immuno-oncology treatment can be based on information consolidated from the results of multiple assays. For example, the following signatures may be selected from categories in Table 1:
a) IFNG Signature: upregulated or not
b) Immune Inflamed OR Immune Excluded OR Immune Desert
c) Immune Escape (or Immune Exhausted): upregulated or not
d) T cell Trafficking: upregulated or not In some embodiments, predicting a response to immuno-oncology treatment can use information consolidated from the results of additional assays, including one or more of a T cell receptor (TCR) assay, a tumor mutation load or burden (TMB) assay, a microsatellite instability (MSI) assay, a microbiome assay and a methylation assay.

In some embodiments, T cell receptor (TCR) assay may be performed on the test sample. TCR assays available from ThermoFisher Scientific include Oncomine™ TCR Beta-SR Assay, RNA (Cat. #A39359), Oncomine™ TCR Beta-SR Assay, DNA (Cat. #A39072) and Oncomine™ TCR Beta-LR Assay (Cat. #A35386). Exemplary methods for TCR beta assay for RNA/cDNA, both long read ("LR") and short read ("SR") assays are described in U.S. Pat. Appl. Publ. No. 2018/0208984, published Jul. 26, 2018, incorporated by reference herein in its entirety. Exemplary methods for TCR beta assay for genomic DNA, short read ("SR") assay are described in U.S. Pat. Appl. Publ. No. 2019/0085374, published Mar. 21, 2019, incorporated by reference herein in its entirety. Exemplary methods for using the TCR assays to measure TCR convergence and haplotype are described in PCT application number PCT/US2019/023731, filed Mar.

22, 2019, incorporated by reference herein in its entirety. Among other metrics, the TCR assay may provide an estimate of clonality, convergence, identify the haplotype of the TRB locus, as indicated by the following, and allow for longitudinal tracking of T cell repertoire features:
   a) Clonal expansion: Evenness, i.e. normalized Shannon entropy. Values range from 0 to 1. An evenness value of 1 indicates that each T cell clone is present at an equal frequency in a sample. Evenness less than 1 indicates clonal expansion.
   b) TCR convergence: A T cell repertoire feature that may indicate the immunogenicity of a tumor. Expressed as the aggregate frequency of T cells having a convergent TCR (see PCT/US2019/023731).
   c) TRB locus haplotype (see Looney et al., "Haplotype Analysis of the TRB locus by TCRB Repertoire Sequencing," www.biorxiv.org/content/10.1101/406157v1, bioRxiv, September 2018.)

In some embodiments, a tumor mutation load or burden (TMB) assay may be performed on the test sample. In some embodiments, a TMB assay may include one or more features described in U.S. Published App. No. 2018/0165410, incorporated by reference herein in its entirety. TMB assays are available from ThermoFisher Scientific (SKU A37909 for manual library prep and A37910 for automated library prep). The TMB assay may provide numbers of mutations per megabase of coding sequence. Levels of mutations may be set as follows:
   a) Low may be above a number in the range of 5 to 10 nonsynonymous mutations per megabase of coding sequence,
   b) High may be below a number in the range of 10 to 20 nonsynonymous mutations per megabase of coding sequence,
   c) Medium may be an intermediate range between low and high.

In some embodiments, a microsatellite instability (MSI) assay may be performed on the test sample. In some embodiments, a MSI assay may include one or more features described in U.S. patent application No. 62/745,161, filed Oct. 12, 2018, and in U.S. patent application No. 62/785,596, filed Dec. 27, 2018, both of which are incorporated by reference herein in their entirety. The MSI assay may provide MSI scores. The MSI assay may provide a MSI status for the test sample. Categories for the MSI status may be MSI-H (high), MSI-L (low) and MSS (stable).

In some embodiments, a microbiome assay may assay a blood and/or stool sample from the same individual to establish a microbiome status. The microbiome status may include the following:
   a) Presence of one or more microbes predictive of response,
   b) Lack of microbes predictive of response.

In some embodiments, a methylation assay may be performed on the test sample. The methylation assay may provide a methylation status as hypo-methylated or hyper-methylated.

Figure 2:
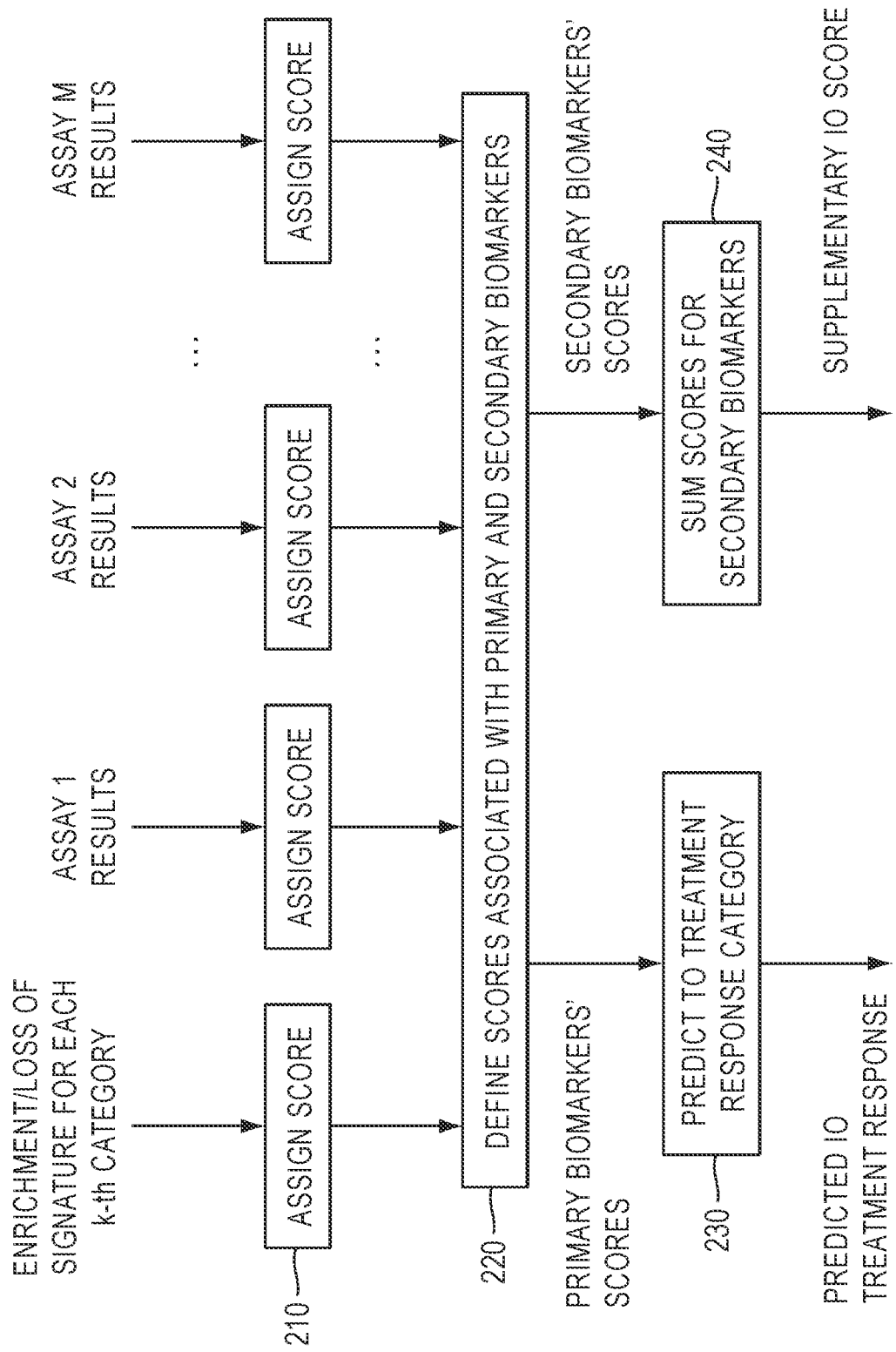
FIG. 2 is a block diagram of a method to predict a response to immuno-oncology treatment using results information from multiple assays, in accordance with an exemplary embodiment.

In some embodiments, predicting a response to immuno-oncology (IO) treatment can apply information from the results of multiple assays to identify a predicted response category for the tumor sample tested. FIG. 2 is a block diagram of an exemplary method to predict a response to immuno-oncology treatment using results information from multiple assays. For example, predicted response categories may include "most likely to respond", "likely to respond" and "least likely to respond". Other numbers and types of predicted response categories may also be used.

In some embodiments, in step 220, one or more biomarkers may be defined as primary and others may be defined as secondary, depending on the tumor type. For example, in colorectal cancer (CRC), MSI status may be defined as a primary biomarker and all other biomarkers may be defined as secondary. For example, for other types of tumors, TMB may be defined as a primary biomarker and all other biomarkers may be defined as secondary.

For example, for CRC samples, the predicted response category of most likely to respond may be assigned to tumor samples with MSI-H. The predicted response category of likely to respond may be assigned to tumor samples with MSI-L. The predicted response category of least likely to respond may be assigned to tumor samples with MSS. For example, for other tumors, the predicted response category of most likely to respond may be assigned to tumor samples with TMB-high. The predicted response category of likely to respond may be assigned to tumor samples with TMB-medium. The predicted response category of least likely to respond may be assigned to tumor samples with TMB-Low.

In some embodiments, combinations of results from various assays may be used to predict a response category. For example, for other tumors, the predicted response category of most likely to respond may be assigned to tumor samples with TMB-high or PD-L1 high. The predicted response category of likely to respond may be assigned to tumor samples with TMB-medium and PD-L1 is absent or medium or low, or PD-L1 is medium, and TMB is absent. The predicted response category of least likely to respond may be assigned to tumor samples with TMB-Low and PD-L1 low, or TMB-Low and PD-L1 absent, or PD-L1 low and TMB absent.

In some embodiments, a score may be assigned to each biomarker depending on the status of the biomarker in step 210. Examples of types of statuses associated with various biomarkers are listed in Table 6. If the status predicts response to immunotherapy, the score=1. If the status predicts lack of response to immunotherapy, the score=−1. If the status is intermediate, the score=0. If the biomarker is not measured, the score=0. Other numbers of scores levels may also be used.

In some embodiments, the score for each biomarker may be assigned a weighting factor. The weighting factor may vary by biomarker. The weighting factor may fall in the range of 0.1 to 100. The weighting factor is multiplied by the score so that biomarkers that are more predictive of response are weighted more heavily compared to biomarkers that are less predictive.

For example, Table 6 lists predicted scores based on the status of each biomarker.

TABLE 6

| Biomarker | Status of Biomarker | Weight | Score |
|---|---|---|---|
| Immune Inflamed | >2-fold increase in gene expression | $X_1$ | +1 |
| | −2 → 2-fold change in gene expression | | 0 |
| | >2-fold decrease in gene expression | | 1 |

TABLE 6-continued

| Biomarker | Status of Biomarker | Weight | Score |
|---|---|---|---|
| IFNG Signature | >2-fold increase in gene expression | $X_2$ | +1 |
| | −2 → 2-fold change in gene expression | | 0 |
| | >2-fold decrease in gene expression | | −1 |
| Immune Excluded | >2-fold increase in gene expression | $X_3$ | +1 |
| | −2 → 2-fold change in gene expression | | 0 |
| | >2-fold decrease in gene expression | | −1 |
| Immune Escape | >2-fold increase in gene expression | $X_4$ | +1 |
| | −2 → 2-fold change in gene expression | | 0 |
| | >2-fold decrease in gene expression | | −1 |
| T cell Trafficking | >2-fold increase in gene expression | $X_5$ | +1 |
| | −2 → 2-fold change in gene expression | | 0 |
| | >2-fold decrease in gene expression | | −1 |
| Immune Desert | >2-fold increase in gene expression | $X_6$ | +1 |
| | −2 → 2-fold change in gene expression | | 0 |
| | >2-fold decrease in gene expression | | −1 |
| Tumor Activity | >2-fold increase in gene expression | $X_7$ | +1 |
| | −2 → 2-fold change in gene expression | | 0 |
| | >2-fold decrease in gene expression | | −1 |
| Tumor Microenvironment (TME) | >2-fold increase in gene expression | $X_8$ | +1 |
| | −2 → 2-fold change in gene expression | | 0 |
| | >2-fold decrease in gene expression | | −1 |
| Immunoscore—ratios of immune markers | >2-fold increase in gene expression | $X_9$ | +1 |
| | −2 → 2-fold change in gene expression | | 0 |
| | >2-fold decrease in gene expression | | −1 |
| Cell type abundance score | High | $X_{10}$ | +1 |
| | Medium | | 0 |
| | Low | | −1 |
| Antigen presentation | High | $X_{11}$ | +1 |
| | Medium | | 0 |
| | Low | | −1 |
| Priming and activation | High | $X_{12}$ | +1 |
| | Medium | | 0 |
| | Low | | −1 |
| Recognition and killing of cancer cells | High | $X_{13}$ | +1 |
| | Medium | | 0 |
| | Low | | −1 |
| Immune Modulation | High | $X_{14}$ | +1 |
| | Medium | | 0 |
| | Low | | −1 |
| Clonal Expansion | Diverse | $X_{15}$ | +1 |
| | Even | | −1 |
| TCR Convergence | Evidence of Convergence | $X_{16}$ | +1 |
| | No evidence of Convergence | | −1 |
| TCR Haplotype | | | |
| TMB | High | $X_{17}$ | +1 |
| | Medium | | 0 |
| | Low | | −1 |
| MSI | MSI-H | $X_{18}$ | +2 |
| | MSI-L | | +1 |
| | No Data | | 0 |
| | MSS | | −1 |
| Microbiome | Species predictive of response | $X_{19}$ | +1 |
| | Lack of species predictive of response | | −1 |
| Methylation | Hyper-methylated | $X_{20}$ | +1 |
| | No Data | | 0 |
| | Hypo-methylated | | −1 |
| HLA LOH | No loss of heterozygosity | $X_{21}$ | +1 |
| | No Data | | 0 |
| | Evidence of loss of heterozygosity | | −1 |
| PD-L1 | High | $X_{22}$ | +1 |
| | Medium | | 0 |
| | Low | | −1 |

In some embodiments, the sum of the scores may be calculated for the secondary biomarkers in step 240 to provide a supplementary IO score. A supplementary IO score may be assigned to each sample within a predicted treatment response category. If the supplementary IO score is high, the sample is predicted to be more likely to respond to immunotherapy. If the supplementary IO score is low, the sample is predicted to be less likely to respond to immunotherapy.

In some embodiments, the weighted sum of the scores may be calculated for the secondary biomarkers in step 240 to provide a supplementary IO score. The weighted sum of the scores is the sum over all the biomarkers of the product of the biomarker weight times the biomarker score. A supplementary IO weighted score may be assigned to each sample within a predicted treatment response category. If the supplementary IO weighted score is high, the sample is more likely to respond to immunotherapy. If the supplementary IO weighted score is low, the sample is less likely to respond to immunotherapy.

For example, Table 7 lists predicted treatment response categories and exemplary conditions for selected results of the multiple assays performed the sample(s) to be classified in the respective category in step 230. The predicted treatment response category is indicated by the primary biomarker or biomarkers.

TABLE 7

| PREDICTED TREATMENT RESPONSE CATEGORY | CONDITIONS |
|---|---|
| Most likely to respond to IO treatment | Primary biomarker is evidence of most likely to respond to IO treatment. The supplementary IO score provides additional prediction within this category, where an individual with a high score is more likely to respond and an individual with a low score is less likely to respond. |
| Likely to respond to IO treatment | Primary biomarker is evidence of likely to respond to IO treatment. The supplementary IO score provides additional prediction within this category, where an individual with a high score is more likely to respond and an individual with a low score is less likely to respond. |
| Least likely to respond to IO treatment | Primary biomarker is evidence of least likely to respond to IO treatment. The supplementary IO score provides additional prediction within this category, where an individual with a high score is more likely to respond and an individual with a low score is less likely to respond. |

According to an exemplary embodiment, there is provided a method, comprising: (a) receiving a plurality of numbers of reads for a plurality of targeted genes of a gene expression assay performed on a test sample. The plurality of targeted genes is organized into a plurality of categories. A $k^{th}$ category of the plurality of categories represents a functional context associated with the targeted genes in the $k^{th}$ category. The $k^{th}$ category has $N_k$ numbers of reads associated with $N_k$ targeted genes of the plurality of targeted genes. For each $k^{th}$ category in the plurality of categories, the method applies the steps: (b) determining a number of reads of the $N_k$ numbers of reads for each $i^{th}$ targeted gene in the $k^{th}$ category; (c) compressing the $N_k$ numbers of reads in the $k^{th}$ category to form a compressed value for the $k^{th}$ category, wherein the compressed value has a reduced amount of data for the $k^{th}$ category for storing in a memory; and (d) comparing the compressed value to a baseline value for the $k^{th}$ category to determine an enrichment or a loss of a signature corresponding to the functional context of the $k^{th}$ category. The compressing step (c) may further include calculating a median value of the $N_k$ numbers of reads for the kth category to form the compressed value, wherein the baseline value is a median baseline value for the comparing step. The compressing step (c) may further include calculating a mean value of the $N_k$ numbers of reads for the $k^{th}$ category to form the compressed value, wherein the baseline value is a mean baseline value for the step of comparing (d). The reduced amount of data for the $k^{th}$ category may have a compression ratio of $N_k:1$. The plurality of categories may include a category for an immune inflamed functional context. The plurality of categories may include a category for an IFNG signature functional context. The plurality of categories may include a category for an immune excluded functional context. The plurality of categories may include a category for an immune escape functional context. The plurality of categories may include a category for a T cell trafficking functional context. The plurality of categories includes a category for an immune desert functional context. The step (d) of comparing the compressed value to a baseline value may further comprise determining a fold change level in the compressed value compared to the baseline value. The method may further comprise assigning a score to the fold change level. A greater than 2-fold increase in the fold change level may be assigned a score value of +1, a greater than 2-fold decrease in the fold change level may be assigned a score value of −1 and fold change levels between a 2-fold decrease and 2 fold increase may be assigned a score value of 0. The method of may further comprise receiving a plurality of assay results from a plurality of assays performed on the test sample, the plurality of assays including one or more of a tumor mutation burden (TMB) assay, a microsatellite instability assay (MSI) and a T cell receptor (TCR) assay. The method may further comprise assigning a score to each assay result provided by the plurality of assays. The plurality of assay results may include a TMB result value of high, medium or low. The method may further comprise assigning score values of +1 to the TMB result value of high, 0 to the TMB result value of medium and −1 to the TMB result value of low. The plurality of assay results may include a MSI result value of MSI-H (high), MSI-L (low), MSS (stable) or "no data". The method may further comprise assigning score values of +2 to the MSI result value of MSI-H (high), +1 to the MSI result value of MSI-L (low), 0 to the MSI result value of "no data" and −1 to the MSI result value of MSS (stable). The plurality of assay results may include a TCR clonal expansion result, including "diverse" and "even," a TCR convergence result, including "evidence of convergence" and "no evidence of convergence," and a TCR haplotype. The method may further comprise assigning score values of +1 to the TCR result of "diverse," −1 for the TCR result of "even," +1 to the TCR convergence result of "evidence of convergence" and −1 to the TCR convergence result of "no evidence of convergence". The method may further include multiplying the score by a weighting factor to give a weighted score. The method may further comprise averaging a second set of $N_k$ numbers of reads for the kth category to give the baseline value for the kth category, wherein the second set of $N_k$ numbers of reads were measured for the targeted genes in normal samples. The method may further comprise transforming the numbers of reads of the second set of $N_k$ numbers of reads to comparable number of read values for a second nucleic acid sequencing device, wherein the second set of $N_k$ numbers of reads were measured using a first nucleic acid sequencing device and the second nucleic acid sequencing device measured the plurality of numbers of reads for the plurality of targeted genes of the gene expression assay performed on the test sample.

According to an exemplary embodiment, there is provided a system, comprising a processor and a memory communicatively connected with the processor, the processor configured to perform a method including: a) receiving a plurality of numbers of reads for a plurality of targeted genes of a gene expression assay performed on a test sample. The plurality of targeted genes is organized into a plurality of categories. A $k^{th}$ category of the plurality of categories represents a functional context associated with the targeted genes in the $k^{th}$ category. The $k^{th}$ category has $N_k$ numbers of reads associated with $N_k$ targeted genes of the plurality of targeted genes. For each $k^{th}$ category in the plurality of categories, the processor applies the steps: (b) determining a number of reads of the $N_k$ numbers of reads for each targeted gene in the $k^{th}$ category; (c) compressing the $N_k$ numbers of reads in the $k^{th}$ category to form a compressed value for the $k^{th}$ category, wherein the compressed value has a reduced amount of data for the $k^{th}$ category for storing in a memory; and (d) comparing the compressed value to a baseline value for the $k^{th}$ category to determine an enrichment or a loss of a signature corresponding to the functional context of the $k^{th}$ category. The compressing step (c) may further include calculating a median value of the $N_k$ numbers of reads for the kth category to form the compressed value, wherein the baseline value is a median baseline value for the comparing step. The compressing step (c) may further include calculating a mean value of the $N_k$ numbers of reads for the kth category to form the compressed value, wherein the baseline value is a mean baseline value for the step of comparing (d). The reduced amount of data for the $k^{th}$ category may have a compression ratio of $N_k:1$. The plurality of categories may include a category for an immune inflamed functional context. The plurality of categories may include a category for an IFNG signature functional context. The plurality of categories may include a category for an immune excluded functional context. The plurality of categories may include a category for an immune escape functional context. The plurality of categories may include a category for a T cell trafficking functional context. The plurality of categories includes a category for an immune desert functional context. The step (d) of comparing the compressed value to a baseline value may further comprise determining a fold change level in the compressed value compared to the baseline value. The method may further comprise assigning a score to the fold change level. A greater than 2-fold increase in the fold change level may be assigned a score value of +1, a greater than 2-fold decrease in the fold change level may be assigned a score value of −1 and fold change levels between a 2-fold decrease and 2 fold increase may be assigned a score value of 0. The method of may further comprise receiving a plurality of assay results from a plurality of assays performed on the test sample, the plurality of assays including one or more of a tumor mutation burden (TMB) assay, a microsatellite instability assay (MSI) and a T cell receptor (TCR) assay. The method may further comprise assigning a score to each assay result provided by the plurality of assays. The plurality of assay results may include a TMB result value of high, medium or low. The method may further comprise assigning score values of +1 to the TMB result value of high, 0 to the TMB result value of medium and −1 to the TMB result value of low. The plurality of assay results may include a MSI result value of MSI-H (high), MSI-L (low), MSS (stable) or "no data". The method may further comprise assigning score values of +2 to the MSI result value of MSI-H (high), +1 to the MSI result value of MSI-L (low), 0 to the MSI result value of "no data" and −1 to the MSI result value of MSS (stable). The plurality of assay results may include a TCR clonal expansion result, including "diverse" and "even," a TCR convergence result, including "evidence of convergence" and "no evidence of convergence," and a TCR haplotype. The method may further comprise assigning score values of +1 to the TCR result of "diverse,"−1 for the TCR result of "even," +1 to the TCR convergence result of "evidence of convergence" and −1 to the TCR convergence result of "no evidence of convergence". The method may further include multiplying the score by a weighting factor to give a weighted score. The method may further comprise averaging a second set of $N_k$ numbers of reads for the $k^{th}$ category to give the baseline value for the $k^{th}$ category, wherein the second set of $N_k$ numbers of reads were measured for the targeted genes in normal samples. The method may further comprise transforming the numbers of reads of the second set of $N_k$ numbers of reads to comparable number of read values for a second nucleic acid sequencing device, wherein the second set of $N_k$ numbers of reads were measured using a first nucleic acid sequencing device and the second nucleic acid sequencing device measured the plurality of numbers of reads for the plurality of targeted genes of the gene expression assay performed on the test sample.

According to an exemplary embodiment, there is provided a non-transitory machine-readable storage medium comprising instructions which, when executed by a processor, cause the processor to perform a method, comprising: a) receiving a plurality of numbers of reads for a plurality of targeted genes of a gene expression assay performed on a test sample. The plurality of targeted genes is organized into a plurality of categories. A $k^{th}$ category of the plurality of categories represents a functional context associated with the targeted genes in the $k^{th}$ category. The $k^{th}$ category has $N_k$ numbers of reads associated with $N_k$ targeted genes of the plurality of targeted genes. For each $k^{th}$ category in the plurality of categories, the processor applies the steps: (b) determining a number of reads of the $N_k$ numbers of reads for each $i^{th}$ targeted gene in the $k^{th}$ category; (c) compressing the $N_k$ numbers of reads in the $k^{th}$ category to form a compressed value for the $k^{th}$ category, wherein the compressed value has a reduced amount of data for the $k^{th}$ category for storing in a memory; and (d) comparing the compressed value to a baseline value for the $k^{th}$ category to determine an enrichment or a loss of a signature corresponding to the functional context of the $k^{th}$ category. The compressing step (c) may further include calculating a median value of the $N_k$ numbers of reads for the $k^{th}$ category to form the compressed value, wherein the baseline value is a median baseline value for the comparing step. The compressing step (c) may further include calculating a mean value of the $N_k$ numbers of reads for the $k^{th}$ category to form the compressed value, wherein the baseline value is a mean baseline value for the step of comparing (d). The reduced amount of data for the $k^{th}$ category may have a compression ratio of $N_k:1$. The plurality of categories may include a category for an immune inflamed functional context. The plurality of categories may include a category for an IFNG signature functional context. The plurality of categories may include a category for an immune excluded functional context. The plurality of categories may include a category for an immune escape functional context. The plurality of categories may include a category for a T cell trafficking functional context. The plurality of categories includes a category for an immune desert functional context. The step (d) of comparing the compressed value to a baseline value may further comprise determining a fold change level in the compressed value compared to the baseline value. The method may further comprise assigning a score to the fold change level. A greater than 2-fold increase in the fold change level may be assigned a score value of +1, a greater than 2-fold decrease in the fold change level may be assigned a score value of −1 and fold change levels between a 2-fold decrease and 2 fold increase may be assigned a score value of 0. The method of may further comprise receiving a plurality of assay results from a plurality of assays performed on the test sample, the plurality of assays including one or more of a tumor mutation burden (TMB) assay, a microsatellite instability assay (MSI) and a T cell receptor (TCR) assay. The method may further comprise assigning a score to each assay result provided by the plurality of assays. The plurality of assay results may include a TMB result value of high, medium or low. The method may further comprise assigning score values of +1 to the TMB result value of high, 0 to the TMB result value of medium and −1 to the TMB result value of low. The plurality of assay results may include a MSI result value of MSI-H (high), MSI-L (low), MSS (stable) or "no data". The method may further comprise assigning score values of +2 to the MSI result value of MSI-H (high), +1 to the MSI result value of MSI-L (low), 0 to the MSI result value of "no data" and −1 to the MSI result value of MSS (stable). The plurality of assay results may include a TCR clonal expansion result, including "diverse" and "even," a TCR convergence result, including "evidence of convergence" and "no evidence of convergence," and a TCR haplotype. The method may further comprise assigning score values of +1 to the TCR result of "diverse,"−1 for the TCR result of "even," +1 to the TCR convergence result of "evidence of convergence" and −1 to the TCR convergence result of "no evidence of convergence". The method may further include multiplying the score by a weighting factor to give a weighted score. The method may further comprise averaging a second set of $N_k$ numbers of reads for the $k^{th}$ category to give the baseline value for the $k^{th}$ category, wherein the second set of $N_k$ numbers of reads were measured for the targeted genes in normal samples. The method may further comprise transforming the numbers of reads of the second set of $N_k$ numbers of reads to comparable number of read values for a second nucleic acid sequencing device, wherein the second set of $N_k$ numbers of reads were measured using a first nucleic acid sequencing device and the second nucleic acid sequencing device measured the plurality of numbers of reads for the plurality of targeted genes of the gene expression assay performed on the test sample.

In some embodiments, an analytics computing server/node/device can be configured to implement the methods described herein and report results to a user. In some embodiments, the analytics computing server/node/device may include one or more features described in U.S. Pat. Appl. Publ. No. 2016/0026753, published Jan. 28, 2016, incorporated by reference herein in its entirety.

In various embodiments, nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, fluorescent-based detection systems, single molecule methods, etc.

Figure 3:
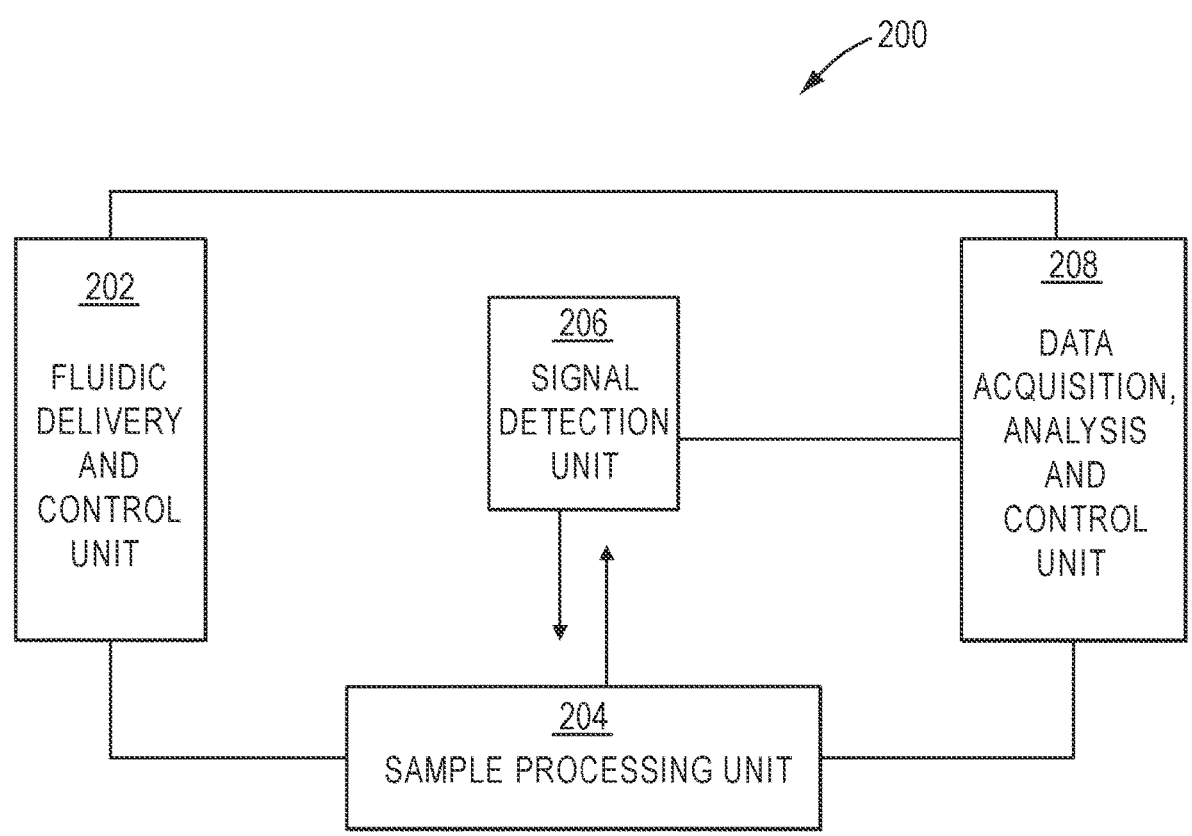
FIG. 3 is a block diagram of an exemplary system for reconstructing a nucleic acid sequence, in accordance with various embodiments.

Various embodiments of nucleic acid sequencing platforms, such as a nucleic acid sequencer, can include components as displayed in the block diagram of FIG. 3. According to various embodiments, sequencing instrument 200 can include a fluidic delivery and control unit 202, a sample processing unit 204, a signal detection unit 206, and a data acquisition, analysis and control unit 208. Various embodiments of instrumentation, reagents, libraries and methods used for next generation sequencing are described in U.S. Patent Application Publication No. 2009/0127589 and No. 2009/0026082. Various embodiments of instrument 200 can provide for automated sequencing that can be used to gather sequence information from a plurality of sequences in parallel, such as substantially simultaneously.

In various embodiments, the fluidics delivery and control unit 202 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 204 can include a sample chamber, such as flow cell, a substrate, a micro-array, a multi-well tray, or the like. The sample processing unit 204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 206 can include an imaging or detection sensor. For example, the imaging or detection sensor can include a CCD, a CMOS, an ion sensor, such as an ion sensitive layer overlying a CMOS, a current detector, or the like. The signal detection unit 206 can include an excitation system to cause a probe, such as a fluorescent dye, to emit a signal. The expectation system can include an illumination source, such as arc lamp, a laser, a light emitting diode (LED), or the like. In particular embodiments, the signal detection unit 206 can include optics for the transmission of light from an illumination source to the sample or from the sample to the imaging or detection sensor. Alternatively, the signal detection unit 206 may not include an illumination source, such as for example, when a signal is produced spontaneously as a result of a sequencing reaction. For example, a signal can be produced by the interaction of a released moiety, such as a released ion interacting with an ion sensitive layer, or a pyrophosphate reacting with an enzyme or other catalyst to produce a chemiluminescent signal. In another example, changes in an electrical current can be detected as a nucleic acid passes through a nanopore without the need for an illumination source.

In various embodiments, data acquisition analysis and control unit 208 can monitor various system parameters. The system parameters can include temperature of various portions of instrument 200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 200 can be used to practice variety of sequencing methods including ligation-based methods, sequencing by synthesis, single molecule methods, nanopore sequencing, and other sequencing techniques.

In various embodiments, the sequencing instrument 200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 200 can obtain the sequence information from a single nucleic acid molecule or from a group of substantially identical nucleic acid molecules.

In various embodiments, sequencing instrument 200 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, R, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

Those skilled in the art may appreciate from the foregoing description that the present teachings may be implemented in a variety of forms, and that the various embodiments may be implemented alone or in combination. Therefore, while the embodiments of the present teachings have been described in connection with particular examples thereof, the true scope of the embodiments and/or methods of the present teachings should not be so limited since other modifications will become apparent to the skilled practitioner upon a study of the drawings, specification, and following claims.

What is claimed is:

1. A non-transitory machine-readable storage medium comprising instructions which, when executed by a processor, cause the processor to perform a method, comprising:
    receiving a plurality of numbers of reads for a plurality of targeted genes of a gene expression assay performed on a test sample, wherein the plurality of targeted genes are organized into a plurality of categories, wherein $N_k$ targeted genes in a $k^{th}$ category are associated with a functional context, wherein $N_k$ numbers of reads correspond to the $N_k$ targeted genes in the $k^{th}$ category;
    for each $k^{th}$ category in the plurality of categories:
        determining a number of reads for each targeted gene of the $N_k$ targeted genes in the $k^{th}$ category to produce the $N_k$ numbers of reads corresponding to the $N_k$ targeted genes;
        compressing the $N_k$ numbers of reads in the $k^{th}$ category to form a compressed value for the $k^{th}$ category, wherein the compressed value comprises a median value of the $N_k$ numbers of reads for the $k^{th}$ category;
        comparing the compressed value to a baseline value for the $k^{th}$ category to determine an enrichment or a loss of a signature corresponding to the functional context associated with the $k^{th}$ category, wherein the baseline value is a median baseline value;
        assigning a score to the comparison of the compressed value to the baseline value for each $k^{th}$ category to form a plurality of comparison scores;
    receiving one or more assay results from one or more assays performed on the test sample, the assays including one or more of a tumor mutation burden (TMB) assay, a microsatellite instability assay (MSI) and a T cell receptor (TCR) assay;
    assigning an assay result score to each assay result to form one or more assay result scores; and
    applying weighting factors to the comparison scores and the assay result scores to form a plurality of weighted scores and one or more weighted assay result scores.

2. The non-transitory machine-readable storage medium of claim 1, wherein the method further comprises predicting a response to an immuno-oncology treatment based on the plurality of weighted scores and the one or more weighted assay result scores.

3. The non-transitory machine-readable storage medium of claim 1, wherein the compressing further comprises calculating a mean value of the $N_k$ numbers of reads for the $k^{th}$ category to form the compressed value, wherein the baseline value is a mean baseline value.

4. The non-transitory machine-readable storage medium of claim 1, wherein a reduced amount of data for the $k^{th}$ category has a compression ratio of $N_k$:1.

5. The non-transitory machine-readable storage medium of claim 1, wherein the plurality of categories includes a category for an immune inflamed functional context.

6. The non-transitory machine-readable storage medium of claim 1, wherein the plurality of categories includes a category for an IFNG signature functional context.

7. The non-transitory machine-readable storage medium of claim 1, wherein the plurality of categories includes a category for an immune excluded functional context.

8. The non-transitory machine-readable storage medium of claim 1, wherein the plurality of categories includes a category for an immune escape functional context.

9. The non-transitory machine-readable storage medium of claim 1, wherein the plurality of categories includes a category for a T cell trafficking functional context.

10. The non-transitory machine-readable storage medium of claim 1, wherein the plurality of categories includes a category for an immune desert functional context.

11. The non-transitory machine-readable storage medium of claim 1, wherein the step of comparing the compressed value to a baseline value further comprises determining a fold change level in the compressed value compared to the baseline value.

12. The non-transitory machine-readable storage medium of claim 11, wherein the step of assigning a score to the comparison comprises assigning the score to the fold change level.

13. The non-transitory machine-readable storage medium of claim 12, wherein a greater than 2-fold increase in the fold change level is assigned a score value of +1, a greater than 2-fold decrease in the fold change level is assigned a score value of −1 and fold change levels between the 2-fold decrease and the 2-fold increase are assigned a score value of 0.

14. The non-transitory machine-readable storage medium of claim 1, wherein the one or more assay results includes a TMB result value of high, medium or low, further comprising assigning score values of +1 to the TMB result value of high, 0 to the TMB result value of medium and −1 to the TMB result value of low.

15. The non-transitory machine-readable storage medium of claim 1, wherein the one or more assay results includes a MSI result value of MSI-H (high), MSI-L (low), MSS (stable) or "no data", further comprising assigning score values of +2 to the MSI result value of MSI-H (high), +1 to the MSI result value of MSI-L (low), 0 to the MSI result value of "no data" and −1 to the MSI result value of MSS (stable).

16. The non-transitory machine-readable storage medium of claim 1, wherein the one or more assay results includes a TCR clonal expansion result of "diverse" or "even", a TCR convergence result of "evidence of convergence" or "no evidence of convergence", and a TCR haplotype result, further comprising assigning score values of +1 to the TCR clonal expansion result of "diverse,"−1 to the TCR clonal expansion result of "even," +1 to the TCR convergence result of "evidence of convergence" and −1 to the TCR convergence result of "no evidence of convergence".

17. The non-transitory machine-readable storage medium of claim 1, wherein the method further comprises averaging a second set of $N_k$ numbers of reads for the $k^{th}$ category to give the baseline value for the $k^{th}$ category, wherein the second set of $N_k$ numbers of reads correspond to the plurality of targeted genes in normal samples.

18. A method, comprising:
receiving a plurality of numbers of reads for a plurality of targeted genes of a gene expression assay performed on a test sample, wherein the plurality of targeted genes are organized into a plurality of categories, wherein $N_k$ targeted genes in a $k^{th}$ category are associated with a functional context, wherein $N_k$ numbers of reads correspond to the $N_k$ targeted genes in the $k^{th}$ category;
for each $k^{th}$ category in the plurality of categories,
determining a number of reads for each targeted gene of the $N_k$ targeted genes in the $k^{th}$ category to produce the $N_k$ numbers of reads corresponding to the $N_k$ targeted genes;
compressing the $N_k$ numbers of reads in the $k^{th}$ category to form a compressed value for the $k^{th}$ category, wherein the compressed value comprises a median value of the $N_k$ numbers of reads for the $k^{th}$ category;
comparing the compressed value to a baseline value for the $k^{th}$ category to determine an enrichment or a loss of a signature corresponding to the functional context associated with the $k^{th}$ category, wherein the baseline value is a median baseline value;
assigning a score to the comparison of the compressed value to the baseline value for each $k^{th}$ category to form a plurality of comparison scores;
receiving one or more assay results from one or more assays performed on the test sample, the assays including one or more of a tumor mutation burden (TMB) assay, a microsatellite instability assay (MSI) and a T cell receptor (TCR) assay;
assigning an assay result score to each assay result to form one or more assay result scores; and
applying weighting factors to the comparison scores and the assay result scores to form a plurality of weighted scores and one or more weighted assay result scores.

19. The method of claim 18, further comprising predicting a response to an immuno-oncology treatment based on the plurality of weighted scores and the one or more weighted assay result scores.

20. The method of claim 18, wherein the step of assigning a score to the comparison comprises:
determining a fold change level in the compressed value compared to the baseline value; and
assigning the score to the fold change level.

* * * * *